(12) United States Patent
Scherer et al.

(10) Patent No.: US 6,465,658 B2
(45) Date of Patent: Oct. 15, 2002

(54) PROCESS FOR THE PREPARATION OF N,N'-CARBONYLDIAZOLES AND AZOLIDE SALTS

(75) Inventors: Johannes Scherer, Leverkusen; Alexander Klausener, Pulheim; Robert Söllner, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/907,320

(22) Filed: Jul. 17, 2001

(65) Prior Publication Data

US 2002/0111497 A1 Aug. 15, 2002

(30) Foreign Application Priority Data

Jul. 19, 2000 (DE) .......................................... 100 35 011

(51) Int. Cl.[7] ..................... C07D 249/08; C07D 233/60
(52) U.S. Cl. ............................... 548/266.8; 548/313.7; 548/335.1; 548/365.1
(58) Field of Search .................... 548/266.8, 313–7, 548/335.1, 365.1

(56) References Cited

U.S. PATENT DOCUMENTS 5,149,707 A 9/1992 Bartroli et al. ............. 514/396

FOREIGN PATENT DOCUMENTS

| DE | 1033210 | 7/1958 |
|----|---------|--------|
| EP | 0 692 476 | 1/1996 |
| WO | 98/31672 | 7/1998 |
| WO | 00/06551 | 2/2000 |

OTHER PUBLICATIONS

G. Ciamician; P. Magnaghi: "Sull'azione del cloruro di carbonile sul composto potassico del pirrolo" Gazzetta Chimica Italiana, Bd. 15, 1885, Seiten 283–289, XP001029275 Seite 283 & Database Crossfire Beilstein Online! Beilstein Institut zur Forderung der Chemischen Wissenschaften, Frankfurt am Main, DE; Zusammenfassung.

Frenzel A et al: "Indol–1–yl– und Pyrrol–1–yl–substituierte Verbindungen des Siliciums und Phosphors" Journal of Organometallic Chemistry, Elsevier–Sequoia S.A. Lausanne, Ch, Bd. 514, Nr. 1, Jul. 17, 1996, Seiten 281–286, XP004035953 ISSN: 0022–328X Seite 282.

Database Crossfire Beilstein Online! Beilstein Institut zur Forderung der Chemischen Wissenchaften, Frankfurt am Main, DE; Database accession No. 81419 XP002180456 Zusammenfassung & Alexander et al.: J. Amer. Chem. Soc., Bd. 72, 1950, Seite 2760.

F. Liebner et al.: "synthese von fungicid wirksamen (1H–1, 2,4–Triazol–1–yl–methyl)silanen und—siloxanen" Liebigs Ann. Chem., Bd. 2, 1994, Seiten 145–150, XP001019263 Seite 147, linke Spalte, Absatz 4.

J. Am. Chem. Soc., vol. 102, Jun. 4, 1980, pp. 4182–4192, James P. Collman, John I. Braumann, Kenneth M. Doxsee, Thomas R. Halbert, Edward Bunnenberg, Robert E. Linder, Gerd N. LaMar, John Del Gaudio, George Land and K. Spartallan, Synthesis and Characterization of "Tailed Picket Fence" Porphyrins.

*Primary Examiner*—Joseph K. McKane
*Assistant Examiner*—Kamal Saeed
(74) *Attorney, Agent, or Firm*—Joseph C. Gil; Richard E. L. Henderson; Godfried R. Akorli

(57) ABSTRACT

This invention relates to the preparation of N,N'-carbonyldiazoles in a particularly advantageous manner by reacting corresponding azolide salts with phosgene in an aromatic compound or an ether as solvent. The azolide salts are preferably prepared by a novel process from an azole that is reacted with a compound of the formula $M'R^7$ or $MgR^8Z'$ in the presence of a solvent.

8 Claims, No Drawings

PROCESS FOR THE PREPARATION OF N,N'-CARBONYLDIAZOLES AND AZOLIDE SALTS

BACKGROUND OF THE INVENTION

The present invention relates to improved processes for the preparation of N,N'-carbonyldiazoles by reaction of azolide salts with phosgene and for the preparation of azolide salts.

It is already basically known that N,N'-carbonyldiazoles can be obtained if azoles are reacted with phosgene (see DE-B 10 33 210, Chem. Ber. 96, 3374 (1963), Org. Synth. Coll. Vol. IV, 201–204 (1968), and EP-A 692,476).

It is disadvantageous in all these processes that half of the azole employed is consumed as scavenger for the hydrogen chloride formed, and therefore only a maximum of 50% of the azole employed can be converted into the desired carbonyidiazole. This is a severe disadvantage, since azoles are expensive products and large azole consumption thus causes high production costs. Furthermore, the azole hydrochlorides are partially obtained in the form of a tacky precipitate, which can be separated off from the carbonyidiazole prepared only with difficulty. Finally, the azole hydrochloride formed as by-product must be disposed of, which causes additional costs.

The process for the synthesis of N,N'-carbonyidiimidazole in accordance with U.S. Pat. No. 4,965,366 attempts to avoid these disadvantages by reacting imidazole with chlorotrimethylsilane in a first reaction step to give trimethylsilylimidazole. An amine (for example, 1,2-diaminoethane) is added at this step in order to scavenge the hydrogen chloride, and the resultant amine hydrochloride is filtered off and either fed to recovery of the amine or disposed of. The trimethylsilylimidazole formed in the reaction furthermore has to be purified by distillation before the further reaction. In the next step, the trimethylsilylimidazole is reacted with phosgene. In this reaction, chlorotrimethylsilane is re-formed, and can, after purification, be reused in the reaction. Disadvantages in this process are the many synthesis and purification steps and the fact that chlorotrimethylsilane is difficult to handle due to its hygroscopic and corrosive properties. In total, three assistants have to be employed for this N,N-carbonyldiimidazole synthesis, namely chlorotrimethylsilane, 1,2-diaminoethane, and sodium hydroxide solution. In addition, the amine, the imidazole, and the solvent required for the trimethylsilylimidazole synthesis have to be dried in a complex procedure.

SUMMARY OF THE INVENTION

A process has now been found for the preparation of N,N'-carbonyl-diazoles of the formula (I)

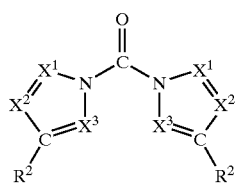

(I)

in which
$X^1$, $X^2$, and $X^3$ independently of one another are each $CR^1$ or nitrogen,
where $R^1$ is hydrogen or $C_1$–$C_6$-alkyl, and
$R^2$ is hydrogen, or in which
X2 is as defined above, and
$X^1$ and $X^3$ are $CR^1$, where the $R^1$ of each $X^1$ is hydrogen or $C_1$–$C_6$-alkyl, and the $R^1$ of each $X^3$, together with $R^2$ of the same diazole ring, forms a —CH=CH—CH=CH— bridge, comprising reacting azolide salts of the formula (II)

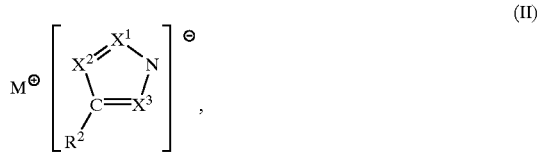

(II)

in which
$M^\oplus$ is an equivalent of an alkali metal or alkaline earth metal cation or a quaternary onium ion of the formula (III)

[Y $R^3R^4R^5R^6$]$^\oplus$   (III), in which
Y is phosphorus or nitrogen, and
$R^3$, $R^4$, $R^5$, and $R^6$ independently of one another are each $C_1$–$C_{20}$-alkyl, phenyl, benzyl, or ethylbenzyl, and the other symbols are as defined for the formula (I), with phosgene in an aromatic compound or an ether as solvent.

DETAILED DESCRIPTION OF THE INVENTION

Preferably in the formulas (I) and (II), $X^1$ and $X^2$, independently of one another, are CH, N, or $CCH_3$, $X^3$ is CH, and $R^2$ is hydrogen, or $X^1$ is CH, $X^2$ is CH, N, or $CCH_3$, and $X^3$ is $CR^1$, where $R^1$ and $R^2$ together form a —CH=CH—CH=CH— bridge.

In the formula (II), $M^\oplus$ is preferably one mol of lithium, sodium, or potassium cations or ½ mol of magnesium cations or 1 mol of a quaternary onium ion of the formula (III), where Y is phosphorus or nitrogen and $R^3$, $R^4$, $R^5$, and $R^6$ are $C_1$–$C_8$-alkyl, or $R^3$, $R^4$, and $R^5$ are $C_1$–$C_6$-alkyl and $R^6$ is $C_4$–$C_{20}$-alkyl, phenyl, benzyl, or ethyl. In particular, $M^\oplus$ is 1 mol of lithium, sodium, or potassium cations.

Particular preference is given to the use of sodium imidazolide or potassium imidazoline or the corresponding 1,2,4-triazolides, pyrazolides, or benzimidazolides, and particular preference is given to the preparation of N,N'-carbonyidiimidazole, N,N'-carbonyldi(1,2,4-triazole), N,N'-carbonyl-dipyrazole, or N,N'-carbonyldibenzimidazole.

In the process according to the invention, from 0.25 to 0.60 mol, for example, of phosgene can be employed per mole of azolide salt of the formula (II). This amount is preferably from 0.45 to 0.55 mol.

Suitable solvents are aromatic compounds, such as benzene, toluene, xylenes, monochlorobenzene, dichlorobenzenes and trichlorobenzenes, and ethers, such as acyclic and cyclic mono- and oligoethers, for example, diethyl ether diisopropyl ether, methyl tert-butyl ether, dibutyl ether, ethylene glycol dimethyl ether, diethylene glycol dimethyl ether, triethylene glycol dimethyl ether, tetrahydrofuran, 2-methyltetrahydrofuran, and dioxane. It is also possible to employ mixtures of these solvents with one another. Preference is given to 2-methyltetrahydrofuran and aromatic solvents, particularly benzene, toluene, xylenes, monochlorobenzene, dichlorobenzenes, and mixtures of these solvents. The preferred solvents can be dried in a simple manner, for example, by azeotropic distillation. A water content of the solvent of less than 0.1% is preferred.

The process according to the invention can be carried out, for example, at temperatures in the range from 10 to 120° C. Preference is given to temperatures in the range from 20 to 110° C., particularly those in the range from 40 to 100° C. The reaction temperature is preferably selected at least sufficiently high that the N,N'-carbonyldiazole of the formula (I) formed does not precipitate during the reaction.

Azolide salts of the formula (II) are accessible, for example, in accordance with J. Am. Chem. Soc. 102, 4182 or EP-A 352,352. However, these processes are inconvenient and complex since either reagents which are difficult to handle are required (for example sodium hydride or butyllithium) or the azolide salt must be isolated and purified. However, a particularly favorable process for the preparation of azolide salts of the formula (II) has also been found, the details of which are described below. In the process according to the invention for the preparation of N,N'-carbonyldiazoles of the formula (I), azolide salts of the formula (II) that have been prepared by the process according to the invention for the preparation of azolide salts of the formula (II) are preferably employed. This has the advantage, for example, that the azolide salt of the formula (II) does not have to be isolated but instead can be employed in the form of the reaction mixture obtained in its preparation according to the invention, if desired after removal of the solvent of the formula (VII) by distillation.

It is advantageous to carry out the process according to the invention for the preparation of N,N'-carbonyldiazoles in the presence of a phase-transfer catalyst. Suitable phase-transfer catalysts are, for example, those of the formulas (VIII) to (X):

$$[YR^3R^4R^5R^6]^+ Z^-, \quad (VIII)$$

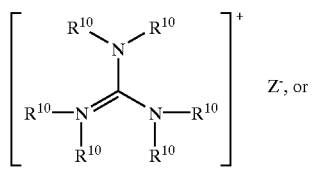

Z⁻, or (IX)

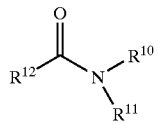

(X)

in which
R³, R⁴, R⁵, and R⁶ are as defined for the formula (III),
R¹⁰ in each case independently of the others is $C_1$–$C_{20}$-alkyl, phenyl, benzyl, or ethylbenzyl,
R¹¹ independently of R¹⁰ is as defined for R¹⁰, or R¹⁰ and R¹¹ together form a (—$CH_2$—)$_n$ bridge, where n is an integer from 1 to 10,
R¹² is NR¹⁰R¹¹, $C_1$–$C_{20}$-alkyl, phenyl, benzyl, orethylbenzyl, and
Z⁻ is Cl⁻, Br⁻, I⁻, OH⁻, $HSO_4^-$, $BF_4^-$, or $PF_6^-$.

Azoles of the formula (IV) (see below) can also be employed as phase-transfer catalysts.

Based on one mole of azolide salt of the formula (II), it is possible to include, for example, from 0.0001 to 0.2 mol, preferably from 0.001 to 0.02 mol, of a phase-transfer catalyst.

In the preparation according to the invention of N,N'-carbonyldiazoles, the second reaction product formed is a chloride of the formula $$M^+Cl^- \quad (XI)$$

in which M⁺ is as defined for the formula (II). This chloride precipitates during the preparation of N,N-carbonyldiazole. The reaction mixture present after the reaction can be worked up, for example, by first separating off the chloride formed, for example, by filtration or siphoning-off the liquid constituents and isolating the prepared N,N'-carbonyldiazole from the filtrate or the siphoned-off liquid either by cooling to from +40 to −70° C., preferably to from +25 to −20° C., but not lower than 5° C. above the solidification point of the solvent used, and filtering off the product that crystallizes out during this operation or stripping off or distilling off the volatile constituents, thereby obtaining the product in solid form.

The preparation according to the invention of N,N'-carbonyldiazoles has the advantage that all the azole or azolide salt employed is available for the formation of N,N'-carbonyidiazole and half is not converted into azole hydrochloride. The yields of N,N'-carbonyidiazole are approximately twice as high as in the direct reaction of azoles with phosgene. Even if phosgene is employed in substoichiometric amounts, a cleaner N,N'-carbonyldiazole is obtained, since unreacted azolide salts are only sparingly soluble in the reaction mixture, in contrast to azoles, and, if they are present therein, are removed from the reaction mixture together with the chloride of the formula (XI). The precise stoichiometric metering of phosgene that is necessary in the direct reaction of azole with phosgene is superfluous in the process according to the invention since product contamination with unreacted azole starting material does not occur.

The present invention furthermore relates to a process for the preparation of azolide salts of the formula (II) comprising reacting an azole of the formula (IV)

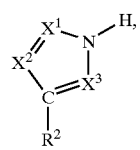

(IV)

in which the symbols used are as defined for the formula (I), with a compound of the formula (V) or of the formula (VI)

$$M'R^7 \quad (V)$$

or $$MgR^8Z' \quad (VI),$$

in which
M' is an equivalent of an alkali metal or alkaline earth metal but is not a quaternary onium ion of the formula (III),
R⁷ is OR⁹, N(R⁹)₂, or ½ $CO_3$, where R⁹ is H, $C_1$–$C_6$-alkyl, or phenyl,
R⁸ is $C_1$–$C_6$-alkyl or phenyl, and
Z' is Cl, Br, or I,
in a solvent.

In the formula (IV), the symbols used preferably have the preferred definitions indicated for the formula (I). In the formula (V), M' is preferably lithium, sodium, or potassium, and R⁷ is preferably OR⁹, where R⁹ is hydrogen or methyl.

In the formula (VI), R⁸ is preferably methyl, ethyl, or phenyl, and Z' is preferably chlorine or bromine.

The solvent can be, for example, one of the solvents mentioned above for the carbonyldiazole synthesis or mixtures thereof with a solvent of the formula (VII)

HR⁷                                                                 (VII), in which R⁷ is as defined for the formula (V) but cannot be ½ CO₃.

If solvents of the formula (VII) are present after the azolide salt preparation, they are distilled off before the reaction with phosgene to give N,N'-carbonyldiazoles of the formula (I).

In preferred embodiments of the process according to the invention for the preparation of azolide salts of the formula (II), the compound of the formula (V) employed is lithium hydroxide, sodium hydroxide, or potassium hydroxide, and the solvent employed is water mixed with chlorobenzene, toluene, or xylene, and the water that is introduced and formed is removed by azeotropic distillation, or the compound of the formula (V) employed is sodium methoxide and the solvent employed is methanol mixed with chlorobenzene or xylene, and the methanol that is introduced and formed is removed by distillation.

The preferred embodiments of the process according to the invention for the preparation of azolide salts of the formula (II) are particularly advantageous over the processes known from the literature since the reaction mixtures that then form, which have been freed from water and methanol, can be employed directly in the process for the preparation of N,N'-carbonyidiazoles of the formula (I), and the separation, work-up, purification, and drying of the azolide salts of the formula (II) are superfluous. In addition, reagents which are expensive and can only be handled with difficulty are generally not required.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

274.4 g of imidazole were introduced into 1000 g of chlorobenzene in a flask fitted with a water separator. 320 g of a 50% strength by weight sodium hydroxide solution were added dropwise. Water was separated out until the distillate no longer separated into two phases. In this way, 231 ml of water were removed from the reaction mixture. 100 ml of chlorobenzene were then distilled off, and the solid components of the reaction mixture were then separated off by filtration and dried, giving 357.2 g of sodium imidazolide (99.2% of theory).

Example 2

In a flask, 180 g of sodium imidazolide (obtained in accordance with Example 1) and 2 g of tributylhexadecylphosphonium bromide were introduced into 1000 g of chlorobenzene which had been dried by incipient distillation. At a temperature of 75–80° C., 98 g of phosgene were passed in over the course of one hour. When the addition was complete, the mixture was stirred at 80° C. for a further 1 hour while a vigorous stream of nitrogen was passed through the flask. The precipitate present was filtered off at 80° C. and rinsed with 100 g of chlorobenzene at 80° C. The filtrate and the washing liquid were combined and cooled to 20° C. The precipitate which deposited was filtered off, rinsed with 100 g of dry chlorobenzene at 20° C., and dried at 60° C. under reduced pressure (50 mbar). 141.1 g of carbonyidiimidazole in the form of colorless crystals having a purity of 98.7% were obtained. This corresponds to a yield of 87.0% of theory.

Examples 3 to 8

The procedure was as in Example 2, but different phase-transfer catalysts were employed. Details can be seen in the following table.

| Example No. | Phase-transfer catalyst | Amount of additive (g) | Yield (isolated) (%) | Purity (%) |
|---|---|---|---|---|
| 3 | Tetraphenylphosphonium bromide | 2 | 76.3 | 96.8 |
| 4 | Tetrabutylammonium bromide | 2 | 70.2 | 97.3 |
| 5 | Hexadecyltrimethyl ammonium bromide | 2 | 68.7 | 95.2 |
| 6 | Tetrabutylurea | 2 | 60.5 | 89.3 |
| 7 | 1,2-Dimethyl-2-imidazolidinone | 2 | 58.7 | 95.0 |
| 8 | Imidazole | 2 | 83.5 | 97.5 |

Example 9

1200 g of chlorobenzene and 272.4 g of imidazole were introduced into a flask fitted with water separator. 320 g of 50% strength by weight sodium hydroxide solution were added dropwise. Water was separated out until the distillate no longer separated into two phases. After 224 ml of water had been separated out in this way, 100 ml of chlorobenzene were removed by distillation, then 2 g of tributylhexadecylphosphonium bromide were added, and 202 g of phosgene were passed in at 80–85° C. over the course of one hour. When the addition was complete, the mixture was stirred at 90° C. for a further 1 hour while a vigorous stream of nitrogen was passed through the flask. The precipitate then present was filtered off at 80° C. and rinsed with 200 g of chlorobenzene at 90° C. The filtrate and the washing liquid were combined and cooled to 0° C. The precipitate which deposited was filtered off, rinsed with 200 g of dry chlorobenzene and dried at 60° C. under reduced pressure (50 mbar). 266 g of carbonyldiimidazole in the form of colorless crystals were obtained in a purity of 97.0%. This corresponded to a yield of 79.5% of theory.

Example 10

272.4 g of imidazole were introduced into 1400 g of chlorobenzene in a flask fitted with column and distillation bridge. 720 g of 30% strength methanolic sodium methoxide solution were added dropwise, and the methanol formed was removed by distillation. 300 ml of chlorobenzene were then removed by distillation, and 2 g of tributylhexadecylphosphonium bromide were added. 202 g of phosgene were passed in at 80–90° C. over the course of one hour. When the addition was complete, the mixture was stirred at 90° C. for a further 1 hour while a vigorous stream of nitrogen was passed through the flask. The precipitate then present was filtered off at 80° C. and rinsed with 200 g of chlorobenzene at 90° C. The filtrate and the washing liquid were combined and cooled to 0° C. The precipitate which deposited was filtered off, rinse with 200 g of dry chlorobenzene and dried at 60° C. under reduced pressure (250 mbar). 234.5 g of carbonyidiimidazole having a purity of 97.4% were thus obtained in the form of colorless crystals. This corresponded to a yield of 72.3% of theory.

Examples 11 to 15

The procedure was as in Example 1, but different azolide salts were employed in corresponding molar amounts. Details can be seen from the following table.

| Example No. | Azolide salt | Product | Yield (isolated) (% of theory) |
| --- | --- | --- | --- |
| 11 | Potassium imidazolide | N,N'-Carbonyldiimidazole | 70 |
| 12 | Lithium imidazolide | N,N'-Carbonyldiimidazole | 60 |
| 13 | Sodium (1,2,4-triazolide) | N,N'-Carbonyldi(1,2,4-triazole) | 69 |
| 14 | Sodium pyrazolide | N,N'-Carbonyldipyrazole | 76 |
| 15 | Sodium benzimidazolide | N,N'-Carbonyldiimidazole | 53 |

Example 16

286.0 g of imidazole were introduced into 1200 g of chlorobenzene in a flask fitted with water separator, and 320 g of 50% strength aqueous sodium hydroxide solution were added dropwise. Water was then separated out until the distillate no longer separated into two phases. After 224 ml of water had been separated out in this way, 100 ml of chlorobenzene were removed by distillation. 202 g of phosgene were subsequently passed in at 80–85° C. over the course of one hour. When the addition was complete, the mixture was stirred at 90° C. for a further 1 hour while a vigorous stream of nitrogen was passed through the flask, and the precipitate then present was filtered off at 80° C. and rinsed with 200 g of chlorobenzene at 90° C. The filtrate and the washing liquid were combined and cooled to 0° C. The precipitate which deposited was filtered off, rinsed with 200 g of dry chlorobenzene, and dried at 60° C. under reduced pressure (50 mbar). 290.6 g of carbonyldiimidazole were thus obtained in the form of colorless crystals having a purity of 97%. This corresponded to a yield of 88% of theory.

Example 17

286.0 g of imidazole were introduced into 1400 g of chlorobenzene in a flask fitted with column and distillation bridge. 720 g of 30% strength methanolic sodium methoxide solution were added dropwise. First methanol was removed by distillation, followed by 300 ml of chlorobenzene. 202 g of phosgene were subsequently passed in at 80–85° C. over the course of one hour. When the addition was complete, the mixture was stirred at 90° C. for a further 1 hour while a vigorous stream of nitrogen was passed through the flask, and the precipitate then present was filtered off at 80° C. and rinsed with 200 g of chlorobenzene at 90° C. The filtrate and the washing liquid were combined and cooled to 0° C. The precipitate which deposited was filtered off, rinsed with 200 g of dry chlorobenzene at 20° C. and dried at 60° C. under reduced pressure (50 mbar). 278.3 g of carbonyidiimidazole were thus obtained in the form of colorless crystals and having a purity of 97.8%. This corresponded to a yield of 84.0% of theory.

What is claimed is:

1. A process for the preparation of N,N'-carbonyldiazoles of the formula (I)

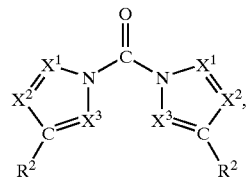

wherein
$X^1$, $X^2$, and $X^3$ independently of one another are each $CR^1$ or nitrogen,
where $R^1$ is hydrogen or $C_1$–$C_6$-alkyl, and
$R^2$ is hydrogen,
or wherein
$X^2$ is as defined above, and
$X^1$ and $X^3$ are $CR^1$, where the $R^1$ of each $X^1$ is hydrogen or $C_1$–$C_6$-alkyl, and the $R^1$ of each $X^3$, together with $R^2$ of the same diazole ring, forms a —CH=CH—CH=CH— bridge,
comprising reacting azolide salts of the formula (II)

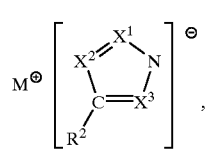

wherein
$M^\oplus$ is an equivalent of an alkali metal or alkaline earth metal cation or a quaternary onium ion of the formula (III)

$$[Y\ R^3\ R^4\ R^5\ R^6]^\oplus \qquad \text{(III)},$$

wherein
Y is phosphorus or nitrogen, and
R$^3$, R$^4$, R$^5$, and R$^6$ independently of one another are each C$_1$–C$_{20}$-alkyl, phenyl, benzyl, or ethylbenzyl, and X$^1$, X$^2$, X$^3$, and R$^2$ are as defined for the formula (I), with phosgene in an aromatic compound or an ether as solvent.

2. A process according to claim 1 wherein
(i) in the formulas (I) and (II), X$^1$ and X$^2$, independently of one another, are CH, N, or CCH$_3$, X$^3$ is CH, and R$^2$ is hydrogen, or X$^1$ is CH, X$^2$ is CH, N, or CCH$_3$, and X$^3$ is CR$^1$, where R$^1$ and R$^2$ together form a —CH═CH—CH═CH— bridge, and
(ii) in the formula (II), M$^+$ is 1 mol of lithium, sodium, or potassium cations or ½ mol of magnesium cations or 1 mol of a quaternary onium ion of the formula (III), where Y is phosphorus or nitrogen and R$^3$, R$^4$, R$^5$, and R$^6$ are C$_1$–C$_8$-alkyl or R$^3$, R$^4$, and R$^5$ are C$_1$–C$_6$-alkyl and R$^6$ is C$_4$–C$_{20}$-alkyl, phenyl, benzyl, or ethyl.

3. A process according to claim 1 wherein from 0.25 to 0.60 mol of phosgene is employed per mole of azolide salt of the formula (II).

4. A process according to claim 1 carried out at temperatures in the range from 10 to 120° C.

5. A process according to claim 1 carried out in the presence of a phase-transfer catalyst.

6. A process according to claim 1 wherein from 0.0001 to 0.02 mol of a phase-transfer catalyst is employed per mole of azolide salt of the formula (II).

7. A process according to claim 1 additionally comprising working up the reaction mixture present after the azolide salt has reacted with phosgene by
(1) separating off the chloride formed in the reaction mixture,
(2) isolating the N,N'-carbonyidiazole from the resultant mixture by cooling to from +40 to −70° C., but not lower than 5° C. above the solidification point of the solvent used, and
(3) filtering off the product that crystallizes out.

8. A process according to claim 1 wherein the N,N'-carbonyidiazole is isolated from the reaction mixture by
(1) separating off the chloride formed in the reaction mixture, and
(2) stripping off or distilling off the volatile constituents to give the N,N'-carbonyidiazole product in solid form.

* * * * *